United States Patent [19]

Schricker

[11] Patent Number: 5,122,512

[45] Date of Patent: Jun. 16, 1992

[54] SWINE GROWTH PROMOTING COMPOSITION

[75] Inventor: Brian R. Schricker, Terre Haute, Ind.

[73] Assignee: Pitman-Moore, Inc., Terre Haute, Ind.

[21] Appl. No.: 242,541

[22] Filed: Sep. 12, 1988

[51] Int. Cl.$^5$ .............................................. A61K 37/36
[52] U.S. Cl. ...................... 514/12; 514/564; 514/565; 426/656; 426/648; 426/442; 426/807
[58] Field of Search ............ 514/12, 564, 565; 426/2, 656, 648, 442, 807

[56] References Cited

U.S. PATENT DOCUMENTS

| | | | |
|---|---|---|---|
| 3,868,467 | 2/1975 | Olson | 426/208 |
| 3,925,568 | 12/1975 | Rao et al. | 426/618 |
| 3,932,608 | 1/1976 | Anderson et al. | 424/54 |
| 3,993,795 | 11/1976 | Mauron et al. | 426/618 |
| 4,172,148 | 10/1979 | Hauck et al. | 424/311 |
| 4,327,118 | 3/1982 | Geeorgen et al. | 426/656 |
| 4,379,177 | 4/1983 | McVoy et al. | 426/656 |
| 4,446,055 | 5/1984 | Shah et al. | 252/351 |
| 4,533,557 | 8/1985 | Maruyama et al. | 426/61 |
| 4,617,155 | 10/1986 | Tanaka et al. | 260/501 |
| 4,701,328 | 10/1987 | Bercovici et al. | 426/2 |

OTHER PUBLICATIONS

Machlin, *Journal of Animal Science.* 35, No. 4, 794-800, 1972.

*Primary Examiner*—F. T. Moezie
*Attorney, Agent, or Firm*—Wendell R. Guffey; Thomas L. Farquer

[57] ABSTRACT

Porcine somatotropin (pST) and dietary lysine are administered in combination in dosages of from about 1-20 mg/swine/day pST and from about 0.9-1.6% by weight dietary lysine to synergistically promote growth, improve weight gain and increase feed utilization efficiency in swine. Administration of the compounds is conveniently accomplished by (1) administering porcine somatotropin (pST) to swine using conventional methods such as injections or implants and (2) feeding the swine a feed composition containing the lysine.

7 Claims, 1 Drawing Sheet

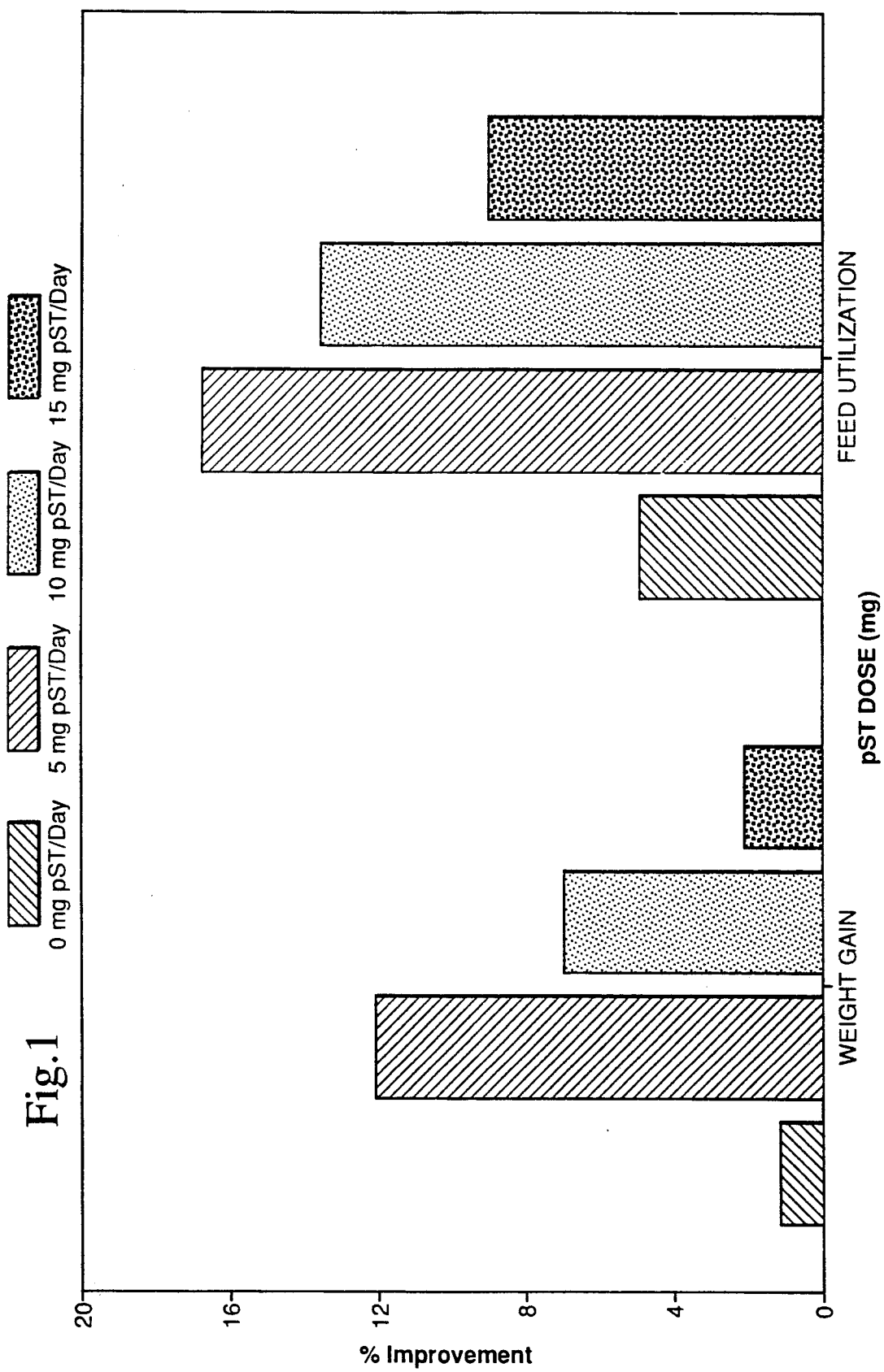

SWINE GROWTH PROMOTING COMPOSITION

This invention relates generally to methods for promoting growth in swine and particularly to a method for using porcine somatotropin in combination with a high level of dietary lysine to synergistically promote growth, improve weight gain and increase feed utilization efficiency in swine.

BACKGROUND OF THE INVENTION

Somatotropin (ST), sometimes referred to as Growth Hormone (GH) in the art, is normally produced by the pituitary throughout an animal's life, although apparently in higher amounts during the pre-adult period. ST is known to promote skeletal growth, nitrogen retention, protein synthesis and to affect glucose and lipid metabolism. Accordingly, ST is recognized as a general anabolic agent.

Although the mechanism of ST activity is not well understood, it has been demonstrated that the administration of exogenous ST of the same species as the test subject markedly increases the rate of growth, weight gain, and meat production in animals and, for porcine somatotropin, improves the chemical composition of the edible meat. See, E. J. Truman, "Some Effects of Pituitary Anterior Growth Hormone On Swine", Thesis; Purdue University (April 1953), ST can be isolated from excised pituitary tissue. See, e.g., C. H. Li, J. Biol. Chem. 211, 55 (1954). ST can also be obtained from genetically engineered microorganisms containing recombinant DNA which specifies the production of ST. See, e.g., P. H. Seeburg, et al., Nature, 276, 795-798 (1978); P. H. Seeburg et al., Nature, 270, 486-494 (1978); J. A. Martial, Science. 205, 602-607 (1979).

Porcine Somatotropin (pST), also referred to in the art as Porcine Growth Hormone (pGH), is a polypeptide synthesized in and secreted from the anterior lobe of the pituitary. The preparation of pST is well known in the art. For example, U.S. Pat. No. 3,201,382 discloses a process for isolating animal somatotropins such as pST from excised pituitary tissue. European Patent Application No. 83305717.7, filed Sep. 26, 1983, with Publication Number 104,920 discloses DNA sequences, recombinant DNA molecules and transformed host suitable for producing pST and European Patent Application No. 83306730.9 filed Apr. 11, 1983, with Publication Number 111,389 discloses DNA sequences and transformed hosts for producing pST.

Lysine is an essential amino acid required for normal animal growth and development. Lysine is present in varying amounts in an animal's diet. However, particularly in animal husbandry, supplementary lysine must be added to an animal's diet to insure proper nutrition.

In addition, high dietary lysine has been used in the art to promote growth, improve weight gain and increase feed utilization efficiency. U.S. Pat. No. 3,868,467 issued to Olson discloses a feed composition comprising high lysine corn to enhance rapid growth of young pigs. The composition also can comprise a further addition of lysine as a separate additive, wherein the lysine comprises up to 0.25% of the total weight of the composition. U.S. Pat. No. 4,172,148 issued to Hauck et al discloses the addition of the trichloroethyl ester of lysine to enhance the growth and feed efficiency of ruminants. However, greater gain and improved feed utilization has been observed with diets containing higher concentrations of lysine: See, Baker et al., Lysine Requirement of Growing Pigs at Two Levels of Dietary Protein, 40 J. Anim. Sci. 851 (1975); Brown et al., Lysine Requirement of the Finishing Pig for Maximum Rate of Gain and Efficiency, 37 J. Anim. Sci. 708 (1973); Kornegay et al., Supplementation of Lysine, Ammonium Polyphosphate and Urea in Diets for Growing-Finishing Pigs, 34 J. Anim. Sci. 55 (1972); Williams et al., The Lysine Requirement of the Growing Boar Versus Barrow, 58 J. Anim. Sci. 657 (1984).

Individually, both somatotropin and high dietary lysine are known to promote growth in swine. However, methods for using known growth promotants in combination to synergistically promote growth are needed; synergistic combinations lower the dosages required for the individual agents and therefore reduce the cost of the materials needed to promote growth.

SUMMARY OF THE INVENTION

It is, therefore, an object of the present invention to provide a method for promoting growth, improving weight gain and increasing feed utilization efficiency in swine.

It is another object of the present invention to provide a method for synergistically promoting growth, improving weight gain and increasing feed utilization efficiency in swine.

It is another object of the present invention to provide a method for reducing the cost of the materials needed to promote growth, improve weight gain and increase feed utilization efficiency in swine.

These and other objects are achieved by administering porcine somatotropin (pST) and high dietary lysine in combination to synergistically promote growth, improve weight gain and increase feed utilization efficiency in swine. Administration of the compounds is conveniently accomplished by (1) administering porcine somatotropin (pST) to swine using conventional methods such as injections or implants and (2) feeding the swine a diet containing lysine in amounts sufficient to, in combination with pST, synergistically promote growth, improve weight gain and increase feed utilization efficiency.

In the preferred embodiment, pST is administered to the swine in dosages of from about 1-20 mg/swine/day, preferably 3-6 mg/swine/day, and lysine is fed to the swine in amounts of from about 0.9-1.6% by weight dietary lysine, preferably from about 1.1-1.4%, to synergistically promote growth, improve weight gain and increase feed utilization efficiency in the swine.

Other objects, advantages, and novel features of the present invention will become apparent from the following detailed description of the invention.

DESCRIPTION OF DRAWINGS

FIG. 1 shows the percent improvement in weight gain and feed utilization efficiency due to the administration of pST and high dietary lysine in combination as compared to pST and lower dietary lysine.

DETAILED DESCRIPTION OF THE INVENTION

The term "high dietary lysine" as used herein means diets containing lysine at about 0.9% by weight or higher.

According to the present invention, porcine somatotropin (pST) and high dietary lysine are administered in combination to swine to synergistically promote growth, improve weight gain and increase feed utilization efficiency in the swine.

pST can be obtained from any suitable source. Methods for producing, isolating and purifying native and recombinant pST are well known in the field. pST as used herein includes all proteins having pST activity including natural, recombinant, and mutein proteins having deleted, replaced, or altered amino acid sequences and biologically active fragments thereof.

Although the dosages of pST vary according to the age, size, and character of the particular swine, pST is typically administered to the swine in dosages of from about 1-20 mg/swine/day, preferably from about 3-6 mg/swine/day.

pST according to the present invention can be administered to the swine in any acceptable manner including by injection, using an implant, and the like. Injections and implants are preferred because they permit precise control of the timing and dosage levels used for administration. pST according to the present invention is preferably administered parenterally. As used herein, parenteral administration means by intravenous, subcutaneous, intramuscular, or intraperitoneal injection, or by subcutaneous implant.

When administered by injection, pST according to the present invention can be administered to the swine in an injectable formulation containing any biocompatible and pST compatible carrier such as various vehicles, adjuvants, additives, and diluents. pST according to the present invention is added to the carrier in amounts sufficient to supply from about 1-20 mg/swine to the swine when injected. Preferably, pST according to the present invention is added to a buffer containing about 0.4-0.5 M arginine hydrochloride in amounts sufficient to supply from about 3-6 mg/swine.

Aqueous vehicles such as water having no nonvolatile pyrogens, sterile water, and bacteriostatic water are also suitable to form injectable pST solutions. In addition to these forms of water, several other aqueous vehicles can be used. These include isotonic injection compositions that can be sterilized such as sodium chloride, Ringer's, dextrose, dextrose and sodium chloride, and lactated Ringer's. Addition of water-miscible solvents, such as methanol, ethanol, or propylene glycol generally increases solubility and stability of pST in these vehicles.

Nonaqueous vehicles such as cottonseed oil, sesame oil, or peanut oil and esters such as isopropyl myristate may also be used as solvent systems for pST compositions.

Additionally, various additives which enhance the stability, sterility, and isotonicity of the composition including antimicrobial preservatives, antioxidants, chelating agents, and buffers can be added. Any vehicle, diluent, or additive used would, however, have to be biocompatible and compatible with pST according to the present invention. Preferably, pST is administered in a buffer containing about 0.4-0.5 M arginine hydrochloride.

pST according to the present invention can be administered to the swine in the form of a slow-release subcutaneous implant which is inserted beneath the skin of the swine. The implant can take the form of a pellet which slowly dissolves after being implanted in the swine or a biocompatible and swine compatible delivery module well known to those skilled in the art. Such well known dosage forms are designed such that the active ingredients are slowly released over a period of several days to several weeks. The implant is designed to deliver from about 1-20 mg/swine/day, preferably from about 3-6 mg/swine/day.

Lysine is an essential amino acid; lysine is required in a swine's diet for normal growth and development. Lysine is present in natural swine foods such as corn and soybeans but often in amounts insufficient to meet the dietary requirements for growing swine. The National Research Council recently (1988) established a dietary lysine requirement of 0.6% for 50-100 kilogram swine. When the diet contains less than the dietary lysine requirement, supplementary lysine is added to the diet. Supplementary lysine can be obtained from any suitable source. Feed grade lysine is available commercially from Biokyowa Inc., 1400 Elbridge Payne, Chesterfield, Mo. 63017. Possibly some diets naturally contain lysine in amounts to, in combination with pST, synergistically promote growth, improved weight gain and increased feed utilization efficiency in swine. However, most generally supplementary lysine must be added to the swine's diet to supply the high dietary lysine required to synergistically promote growth in combination with pST.

Although the dosages of lysine vary according to the age, size, and character of the particular swine, lysine is typically administered to the swine in dosages of from about 0.9-1.6% dietary lysine, preferably from about 1.1-1.4%. In the preferred embodiment, lysine is admixed with the swine's feed in amounts sufficient to supply the required dosages, typically by preparing a feed composition containing from about 0.9-1.6% lysine, preferably about 1.1-1.4% lysine.

Lysine according to the present invention can be administered to the swine in any acceptable manner, preferably orally. Oral administration includes administering lysine in tablets, suspensions, solutions, emulsions, capsules, powders, syrups, feed compositions, and the like. For example, lysine can be blended with ordinary feed compositions. In the preferred embodiment, lysine is administered to the swine by feeding the swine a feed composition containing lysine in amounts sufficient to, in combination with pST, synergistically promote growth, improve weight gain and increase feed utilization efficiency in swine.

When lysine is to be administered in feeds, a feed composition may be prepared containing supplementary lysine and the usual nutritionally-balanced feed containing quantities of carbohydrates, fats, proteins, vitamins and minerals in accordance with the present invention. Some of the usual dietary elements included in feed compositions are grains, such as ground grain and grain byproducts, swine protein substances, such as those found in fish meal and meat scraps, vegetable proteins, like soybean oil meal or peanut oil meal; vitamins and vitamin-containing materials, e.g., vitamin A and D mixtures, riboflavin supplements and other vitamin B complex members; and bone meal and limestone to provide minerals. A type of conventional feed material for use with swine includes corn and soybean meal together with supplementary vitamins, vitamin-containing substances, and minerals if desired. An example of a well known feed compositions useful in the present invention include as disclosed in U.S. Pat. No. 4,320,116 (basic ingredients for feed compositions for swine, piglets, and other swines), incorporated herein by reference. Many other such feed compositions are well known to those skilled in the art.

pST and lysine are administered "in combination" which, as defined herein, includes various schemes designed to administer pST and lysine to swine such that the required synergistic dosages of the compounds are present in the swine at the same time; e.g. (1) implanting a pST prolonged delivery device which delivers the pST over an extended period and feeding lysine to the swine along with its daily feed or (2) injecting pST on a periodic basis and feeding lysine to the swine along with its daily feed.

Since pST and lysine can be administered separately, the present invention also contemplates an article of manufacture in the form of a kit comprising in separate containers in a single package or packages (1) porcine somatotropin (pST) and (2) a lysine supplement suitable for producing a feed composition to be administered in combination with the pST. The kit should contain pST in a form suitable for administration to the animal, i.e. an injectable formulation or an implant and should contain lysine in a form suitable for mixing with conventional feeds to produce a diet containing "high dietary lysine." The lysine supplement could also be fed directly to the animal without mixing it with the animal's feed.

The kit may contain pST in the form of one or more implants or injectable formulation for periodic administration to the animals at a dosage of from about 1-20 mg/swine/day. The kit may also contain a concentrated lysine supplement for mixing or blending with the animal's feed to produce a feed containing the amount of lysine required in the present invention, about 0.9-1.6% by weight dietary lysine.

pST and lysine according to the present invention are used in combination to synergistically promote growth, improve weight gain and increase feed utilization efficiency in swine.

The invention having been generally described, the following examples are given as particular embodiments of the invention and to demonstrate the practice and advantages thereof. It is understood that the examples are given by way of illustration and are not intended to limit the specification or the claims to follow in any manner.

EXAMPLE 1

Seventy-two crossbred barrows were selected for the study on the basis of health and body weight. Pigs were randomly allotted to individual pens and acclimated to the facility approximately two weeks before treatment initiation. During the pre-experimental period all swines received diet 1 depicted in Table 1. Feed and water were offered ad libitum.

The barrows were divided into eight treatment groups of nine barrows per group and administered pST and lysine as shown in Table 2.

Samples were collected from each batch of feed used in the study and, at the end of the study, were composited and analyzed for crude protein, lysine, calcium and phosphorus.

Injectable solutions of pST were prepared in 0.427 M arginine hydrochloride. The arginine hydrochloride was aseptically added to the pST to provide the desired pST concentration. Placebo solutions consisted of the arginine hydrochloride solution alone. All doses were administered in a total volume of 1 ml. The injections were administered intramuscularly in the dorsal neck region using alternate sites for each subsequent injection. A new sterile injection syringe was used for each dosage concentration. All injections were administered between 0800 and 1000 hours on each injection day. The condition of the administration site was monitored on a daily basis and recorded in the study record.

Pigs were weighed and feed intake determined at the initiation of the study, periodically during the study, and on day 56. This data, day 56 feed intake and weight, was used to determine average daily gain, average daily feed intake and feed utilization efficiency. The experiment was conducted as a 2×4 factorial design with pST dose/frequency and dietary lysine serving as main effects. Pen location served as the blocking factor. Initial body weight served as a covariant for production performance data. The results from the experiment are shown in the Table 3. Data were analyzed by analysis of variance (SAS, 1985). The results as percent improvement are shown in FIG. 1.

Referring to Table 3 and FIG. 1, weight gain and feed utilization efficiency were greater when lysine was fed in combination with pST. Average daily gain improved only 1.2% with added dietary lysine in the absence of pST; average daily gain improved 12% with 5 mg pST/day, 7% with 10 mg pST/2 days, and 2% with 15 mg pST/3 days. Feed utilization improved by 5% with added dietary lysine in the absence of pST while improvements were 17, 12 and 8% for the 5 mg/day, 10 mg/2 day and 15 mg/3 day pST treatment combinations, respectively. In addition, the improvements in weight gain and feed utilization are not simply additive but were synergistic.

Obviously many modifications and variations of the present invention are possible in light of the above teachings. It is therefore to be understood that within the scope of the appended claims the invention may be practiced otherwise than as specifically described.

TABLE 1

| Ingredient | Diet Composition | |
| --- | --- | --- |
| | 1 | 2 |
| Ground yellow corn | 74.03 | 73.54 |
| Soybean meal (44% CP) | 21.6 | 21.6 |
| DYNAFOS ® | 2.4 | 2.4 |
| Limestone | 1.0 | 1.0 |
| Salt | 0.4 | 0.4 |
| Vitamin/mineral mix | 0.25 | 0.25 |
| L-lysine.HCl | — | 0.4875 |
| DL-Methionine | 0.18 | 0.18 |
| L-Threonine | 0.14 | 0.14 |
| Calculated Analysis | | |
| Crude protein (%) | 16.0 | 16.0 |
| Lysine (%) | 0.81 | 1.2 |
| Threonine (%) | 0.82 | 0.82 |
| Methionine (%) | 0.48 | 0.48 |
| Cystine (%) | 0.3 | 0.3 |
| ME (kcal/kg) | 3263 | 3263 |
| Ca (%) | 1.0 | 1.0 |
| P (%) | 0.8 | 0.8 |
| Actual Analysis | | |
| Crude protein (%) | 15.5 | 16.8 |
| Ca (%) | 1.1 | 1.16 |
| P (%) | 0.76 | 0.77 |
| Lysine (%) | 0.73 | 1.01 |

TABLE 2

| Treatment Number | Diet | pST Dose/Frequency |
| --- | --- | --- |
| 1 | 1- .8% lysine | 0 mg pST/day |
| 2 | 1- .8% lysine | 5 mg pST/day |
| 3 | 1- .8% lysine | 10 mg pST/2 days |
| 4 | 1- .8% lysine | 15 mg pST/3 days |
| 5 | 2- 1.2% lysine | 0 mg pST/day |
| 6 | 2- 1.2% lysine | 5 mg pST/day |
| 7 | 2- 1.2% lysine | 10 mg pST/2 days |

TABLE 2-continued

| Treatment Number | Diet | pST Dose/Frequency |
|---|---|---|
| 8 | 2- 1.2% lysine | 15 mg pST/3 days |

TABLE 3

Effect of pST and Dietary Lysine on Cumulative Swine Performance

| | pST Dose/Lysine | | | | | | | |
|---|---|---|---|---|---|---|---|---|
| | 0 mg pST | | 5 mg pST | | 10 mg pST | | 15 mg pST | |
| Day | .8% | 1.2% | .8% | 1.2% | .8% | 1.2% | .8% | 1.2% |
| | Average Daily Gain (kg) | | | | | | | |
| 56 | .85 | .86 | .92 | 1.03 | .87 | .93 | .99 | 1.01 |
| | Average Daily Feed (kg) | | | | | | | |
| 56 | 3.49 | 3.40 | 2.86 | 2.69 | 3.04 | 2.89 | 3.44 | 3.24 |
| | Feed/Gain Ratio | | | | | | | |
| 56 | 4.15 | 3.95 | 3.14 | 2.60 | 3.51 | 3.09 | 3.50 | 3.21 |

What is claimed is:

1. A method for synergistically promoting growth, improving weight gain and increasing feed utilization efficiency in swine, comprising:
   administering porcine somatotropin to said swine in amounts of from about 1-20 mg/swine/day; and
   feeding said swine a feed composition containing from about 0.9-1.6% dietary lysine.

2. The method of claim 1 wherein said porcine somatotropin is administered in amounts of from about 3-6 mg/swine/day and said feed composition contains from about 1.1-1.4% dietary lysine.

3. The method of claim 1 wherein said porcine somatotropin is administered parenterally.

4. The method of claim 3 wherein said porcine somatotropin is administered using an implant, said implant further comprising:
   a biocompatible and porcine somatotropin compatible implant material; and
   a growth promoting, weight gain improving and feed utilization increasing amount of said porcine somatotropin.

5. The method of claim 3 wherein said porcine somatotropin is administered in an injectable formulation said injectable formulation further comprising:
   a biocompatible and porcine somatotropin compatible carrier; and
   a growth promoting, weight gain improving and feed utilization increasing amount of said porcine somatotropin.

6. The method of claim 5 wherein said carrier is a buffer containing about 0.4-0.5 M arginine hydrochloride.

7. The method of claim 1 wherein said porcine somatotropin is a recombinant porcine somatotropin.

* * * * *